United States Patent
Era et al.

(10) Patent No.: US 12,150,939 B2
(45) Date of Patent: Nov. 26, 2024

(54) THERAPEUTIC DRUG FOR ECTOPIC OSSIFICATION HAVING MECHANISM TO INHIBIT PAR1

(71) Applicant: NATIONAL UNIVERSITY CORPORATION KUMAMOTO UNIVERSITY, Kumamoto (JP)

(72) Inventors: Takumi Era, Kumamoto (JP); Takayuki Kiboku, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 251 days.

(21) Appl. No.: 17/106,565

(22) Filed: Nov. 30, 2020

(65) Prior Publication Data

US 2021/0161872 A1    Jun. 3, 2021

Related U.S. Application Data

(62) Division of application No. 15/776,152, filed as application No. PCT/JP2016/084101 on Nov. 17, 2016, now abandoned.

(30) Foreign Application Priority Data

Nov. 20, 2015   (JP) ................................ 2015-228232

(51) Int. Cl.
*A61K 31/443* (2006.01)
*A61P 19/08* (2006.01)

(52) U.S. Cl.
CPC ............ *A61K 31/443* (2013.01); *A61P 19/08* (2018.01)

(58) Field of Classification Search
CPC ............................. A61K 31/443; A61P 19/08
See application file for complete search history.

(56) References Cited

U.S. PATENT DOCUMENTS

| | | | |
|---|---|---|---|
| 2014/0378502 A1* | 12/2014 | Riteau | A61K 31/4745 514/292 |
| 2015/0160194 A1 | 6/2015 | Era | |
| 2017/0211070 A1 | 7/2017 | Hino | |

FOREIGN PATENT DOCUMENTS

| | | |
|---|---|---|
| WO | 13039087 A1 | 3/2013 |
| WO | 2015054718 A1 | 4/2015 |
| WO | 2015152183 A1 | 10/2015 |

OTHER PUBLICATIONS

Shen et al., J. Orthop. Res., 32: 1549-1556 (Year: 2014).*

(Continued)

*Primary Examiner* — Jeffrey S Lundgren
*Assistant Examiner* — Anthony Joseph Seitz
(74) *Attorney, Agent, or Firm* — RANKIN, HILL & CLARK LLP (57) ABSTRACT

A pathological mechanism in FOP patients is further revealed, and development of a novel therapeutic drug, therapeutic method, diagnostic method, etc. utilizing an obtained finding is provided. The inventors have found a novel finding that in FOP, ectopic ossification, which occurs by an inflammation due to an injury, etc., is mediated by PAR1 to occur. From this finding, the inventors completed the present invention relating to a drug, etc. characterized by suppressing ectopic ossification in FOP by inhibiting PAR1.

8 Claims, 6 Drawing Sheets

(56) References Cited

OTHER PUBLICATIONS

Shi et al., (2013) Antisense-Oligonucleotide Mediated Exon Skipping in Activin-Receptor-Like Kinase 2: Inhibiting the Receptor That Is Overactive in Fibrodysplasia Ossificans Progressiva. PLoS One 8(7): e69096 (Year: 2013).*

International Search Report dated Feb. 7, 2017 filed in PCT/JP2016/084101.

Hamasaki, Makoto et al., "Pathogenic Mutation of ALK2 Inhibits Induced Pluripotent Stem Cell Reprogramming and Maintenance: Mechanisms of Reprogramming and Strategy for Drug Identification," Stem Cells, Nov. 2012, p. 2437-2449, vol. 30, www.StemCells.com; Cited in Specification.

Fusaki, Noemi et al., "Efficient induction of transgene-free human pluripotent stem cells using a vector based Sendai virus, an RNA virus that does not integrate into the host genome," Proc. Jpn. Acad., Ser B, 2009, p. 348-362, vol. 85 No. 8; Cited in Specification.

Abraham, Linda et al., "Modulation of Osteoblast-like Cell Behavior by Activation of Protease-Activated Receptor-1," Journal of Bone and Mineral Research, 1999, p. 1320-1329, vol. 14 No. 8, Blackwell Science Inc. United Kingdom; Cited in ISR.

Kosoglou, Teddy et al., "No. differences in the pharmacodynamics and pharmacokinetics of the thrombin receptor antagonist vorapaxar between healthy Japanese and Caucasian subjects," Eur J Clin Pharmacol, 2012, p. 291-300, vol. 68, Springer Verlag, Germany; Cited is ISR.

Ando, Takashi et al., "Stimulation of Murine and Human Osteoblast-like Cells with Thrombin Promotes Generation pf MCP-1 from PAR-1 Receptor Through Mapk," J. Jpn. Orthop. Assoc., 2014, p. S1475, 1-PD-5, vol. 88 No. 8; Cited In ISR with translation.

Huang, Chun-Yin et al., "Thrombin Induces Epidermal Growth Factor Receptor Transactivation and CCL2 Expression in Human Osteoblasts," Arthritis & Rheumatism, 2012, p. 3344-3354, vol. 10 No. 64, John Wiley & Sons, USA; Cited in ISR.

Jie, G. et al., "Study on the impact of celecoxib on proliferation of human osteoblasts," Acta Universitatis Medicinalis Anhui, May 2015, p. 608-611, vol. 50 No. 5; Cited in ISR.

Shimakoshi, Y., "The main history of etidronate (EHDP) development in Japan," The Bone, 2005, p. 35-39, vol. 19 No. 1; Cited in ISR.

K. Shen et al., "Activated Protein C (APC) can Increase Bone Anabolism via a Protease-Activated Receptor (PAR) 1/2 Dependent Mechanism: APC Increase Bone Anabolism", Journal of Orthopaedic Research, Dec. 2014, pp. 1549-1556, vol. 32, No. 12, Wiley Periodicals Inc., USA; Cited in EESR; English text.

O. Aisiku et al., "Parmodulins inhibit thrombus formation without inducing endothelial injury caused by vorapaxar", Blood, Mar. 19, 2015, pp. 1976-1985, vol. 125, No. 12, The American Society of Hematology, USA; Cited in EESR; English text.

European Search Report issued on Jun. 28, 2019 for the corresponding European Patent Application No. 16866386.2.

\* cited by examiner

ALP immunostaining

Normal: Normal human skin-derived fibroblasts, FOP: FOP skin-derived fibroblasts

FIG. 8 vehicle

Vorapaxar

FIG. 9

FIG. 10 siLuciferase siPAR1 siALK2-R206H

FIG. 11

THERAPEUTIC DRUG FOR ECTOPIC OSSIFICATION HAVING MECHANISM TO INHIBIT PAR1

TECHNICAL FIELD

The present invention relates to a therapeutic drug for ectopic ossification having a mechanism to inhibit PAR1. The present invention more specifically relates to a drug for treating or preventing ectopic ossification, which is a pathological condition characteristically observed in FOP.

BACKGROUND ART

Fibrodysplasia ossificans progressiva (hereinafter, "FOP") is a disease in which soft tissues and/or muscles throughout a body progressively ossify. Normally, soft tissues do not ossify. FOP is characterized by a phenomenon called ectopic ossification in which soft tissues ossify. Ectopic ossification is caused by an inflammation due to an injury, etc. In FOP, joint mobility in limbs can decrease and a back deformity can be caused, due to progressive ossification.

Recent studies have revealed that FOP is a disease induced by a point mutation on gene in ALK2 (activin receptor-like kinase 2).

That is, ALK2 is a kinase which functions as a single-pass transmembrane receptor of BMP (bone morphogenetic protein). BMP is known as a bone inducing factor. ALK2 is normally activated by binding to BMP in an extracellular region. Activated ALK2 transmits an osteogenic signal to cells. In FOP patients, a point mutation occurs in this ALK2 gene. Therefore, a mutated ALK2 protein called R206H or G356D is generated. These ALK2 mutants are activated without binding to BMP in an extracellular region. Therefore, an osteogenic signal is continually transmitted. As a result, bone induction is abnormally promoted, and thus it has been revealed that ossification of soft tissues, muscles, etc. progresses.

As described above, the pathogenic mechanism of FOP has been revealed. On the other hand, the mechanism of ectopic ossification in FOP has been hardly revealed. Moreover, an effective method for treating FOP has not been established so far.

That is, a therapeutic drug for FOP has been developed, with a focus on a kinase inhibitor targeting ALK2, ALK2 being a pathogenic factor. However, a clinically effective therapeutic drug has not been developed until now.

Originally, osteogenic signal transduction by ALK2 and BMP plays an important role for osteogenesis during normal growth. Because of this, there is a risk that administration of an ALK2 inhibitor to children during their growth period has some adverse effect on normal skeletal formation accompanied with growth. That is, development of a drug having the mechanism to inhibit ALK2 is expected to be effective; however, concern in terms of safety cannot be dismissed.

As described above, a therapeutic drug for FOP which is clinically used has not been developed yet. In addition to this, since ossification is promoted by invasion during a surgery, surgical treatment cannot be carried out. Because of these reasons, an effective method for treating FOP has not been established so far. Therefore, FOP develops from infancy to school age, and patients die by the age of approximately forty due to restrictive respiratory impairment at a high rate. Because of this, FOP is designated as an intractable disease.

CITATION LIST

Patent Literature

PATENT LITERATURE 1: Wo 2013/039087

Non-Patent Literature

NON-PATENT LITERATURE 1: Hamasaki M, Era T. Et al. Stem Cells. 2012 November; 30(11): 2437-49. doi: 10. 1002/stem. 1221.

SUMMARY OF THE INVENTION

Problems to be Solved by the Invention

The inventors studied a method for treating FOP, using iPS cells (induced pluripotent stem cells). As a result, the inventors have revealed that it is difficult to establish iPS cells from dermal fibroblasts from FOP patients (Patent Literature 1, Non-patent Literature 1). From this finding, the inventors have completed an invention relating to a method for screening a substance. However, a fundamental cause of difficulty in establishing iPS cells from dermal fibroblasts from FOP patients has been unclear.

With the above circumstances as background, a subject of the present invention is to clarify the cause of difficulty in establishing iPS cells from dermal fibroblasts from FOP patients, to further reveal a pathological mechanism in FOP patients, and to develop a novel therapeutic drug, therapeutic method, diagnostic method, etc. obtained by using the acquired finding.

Solution to the Problems

As a result of diligent research, the inventors have found that methylation of K4 and K27 of histone H3 decreases in induction of iPS cells of FOP patients.

In association with a reduction in methylation of K27 of histone H3, the inventors have further analyzed a molecular group of which expression specific to FOP increases. As a result, the inventors have identified a novel gene called F2r. F2r is a gene encoding a receptor called protease-activated receptor 1 (PAR1). PAR1 is activated by e.g. thrombin, a blood coagulation factor. Thrombin is a protein which is secreted in large amounts in an injury site.

Based on an increase in F2r expression in FOP, the inventors have thought that ectopic ossification caused by an injury is possibly mediated by PAR1. The inventors have revealed, by verification of the hypothesis, that this hypothesis is confirmed. Accordingly, the inventors have completed the present invention.

The present invention has the following configurations.

The first configuration of the present invention is a drug characterized by treating or preventing ectopic ossification by inhibiting PAR1.

The second configuration of the present invention is the drug according to the first configuration, characterized in that PAR1 is inhibited by an antagonist of PAR1.

The third configuration of the present invention is the drug according to the second configuration, characterized in that the antagonist of PAR1 is ethyl [(1R,3aR,4aR,6R,8aR,9S,9aS)-9-{(1E)-2-[5-(3-fluorophenyl)pyridin-2-yl]ethen-1-yl}-1-methyl-3-oxododecahydronaphtho[2,3-c]furan-6-yl]carbamate or a salt thereof.

The fourth configuration of the present invention is the drug according to the first to third configuration, characterized in that ectopic ossification is a symptom caused by fibrodysplasia ossificans progressiva.

The fifth configuration of the present invention is a method for treating or preventing ectopic ossification by using a drug according to the first to fourth configuration.

Advantageous Effects of the Invention

The present invention has revealed a cause of difficulty in establishing iPS cells from dermal fibroblasts from FOP patients. The present invention has revealed a mechanism of ectopic ossification in FOP patients. Furthermore, the present invention has enabled development of a drug, which can be expected to have an effect of suppressing or preventing ectopic ossification.

DESCRIPTION OF EMBODIMENTS

A drug of the present invention will now be described.

The inventors have found a novel finding by revealing experimental facts described below. According to this finding, in FOP, ectopic ossification, which occurs by an inflammation due to an injury, etc., is mediated by PAR1 to occur.

(1) In FOP-derived fibroblasts, a differentiation to osteoblasts largely progresses and PAR1 expression level largely increases, by BMP6 stimulation in the presence of serum, as compared to those in normal subject-derived fibroblasts.

(2) When a similar experiment as in the above (1) is carried out without serum to remove an effect of e.g. thrombin, which enhances PAR1 signal, existing in serum, an effect of inducing osteoblasts by BMP6 stimulation is dramatically reduced. On the other hand, when stimulation by BMP6 and stimulation by an agonist of PAR1 are provided together, a differentiation to osteoblasts returns to a level equal to that of a case where serum is added.

(3) Furthermore, osteoblast induction by adding BMP6 and TFLLR is strongly suppressed by a PAR1 inhibitor or a PI3K inhibitor, PI3K being activated downstream of PAR1.

(4) In a model mouse which forms a teratoma with use of fibroblasts derived from FOP patients, an increase in bone volume in teratomas is suppressed by a PAR1 inhibitor. In addition, an increase in bone volume in teratomas is suppressed by suppression of PAR1 expression with use of siRNA as in a case of suppression of ALK2 expression.

A drug according to the present invention is based on such finding. The drug of the present invention is characterized by treating or preventing ectopic ossification by inhibiting PAR1. That is, according to the present invention, ectopic ossification is treated, suppressed or prevented by administration of a drug having a mechanism to inhibit PAR1 based on such finding.

In the present invention, ectopic ossification is defined as a phenomenon in which soft tissues ossify by an inflammation due to an injury, etc while the soft tissues normally do not ossify. Ectopic ossification is a clinical state typically observed in FOP. FOP is provided as an example for a purpose of illustration also in the present invention. However, target diseases of the present invention are not limited to FOP. The target diseases of the present invention include, as the target, all diseases having ectopic ossification based on the mechanism led from the above-described finding found by the inventors.

Inhibiting PAR1 is defined as a concept including directly inhibiting PAR1 for example by binding of an antagonist to PAR1, and moreover indirectly inhibiting PAR1 by inhibiting or suppressing an upstream molecule of PAR1.

The drug of the present invention can be used in various dosage forms. The drug of the present invention is preferably in the form of oral preparation such as tablets, capsules or powder. Furthermore, the drug of the present invention can be also in the form of, for example, injectable preparation or transdermal absorption preparation. In addition, a period for which the drug of the present invention can be administered is not particularly limited as long as effectiveness as a drug can be sufficiently exhibited considering for example age, symptoms and dosage forms. The drug of the present invention can be desirably administered for a long period of time. The drug of the present invention can be administered for example continuously for two days or more, preferably continuously for a few months or more, and more preferably continuously for several years or more.

An antagonist of PAR1 is defined as a molecule which blocks or suppresses signal transduction by binding to a receptor of PAR1. The present invention is not limited to a case where an antagonist molecule of PAR1 is included in drug components themselves. That is, in view of a purpose of the present invention, the present invention includes a case where a so-called DDS molecule is one of the components. The DDS molecule exhibits a medicinal effect by a change, in the body, into an antagonist of PAR1, the change caused by e.g. a drug metabolism.

Examples of antagonists of PAR1 include SCH79797 (N3-cyclopropyl-7-[[4-(1-methylethyl)phenyl]methyl]-7H-pyrrolo[3,2-f]quinazoline-1,3-diamine), Vorapaxar (ethyl [(1R,3aR,4aR,6R,8aR,9S,9aS)-9-{(1E)-2-[5-(3-fluorophenyl)pyridin-2-yl]ethen-1-yl}-1-methyl-3-oxododecahydronaphtho[2,3-c]furan-6-yl]carbamate), or salts thereof.

As salts of the antagonists of PAR1, various salt forms can be adopted considering availability, as a medicinal component, such as an improvement of solubility and stability as a drug. In a case of the above-described SCH79797, a salt form which can be adopted is preferably a dihydrochloride (SCH79797 dihydrochloride). In a case of Vorapaxar, a salt form which can be adopted is preferably a sulfate (Vorapaxar sulfate).

When Vorapaxar is used as an example, it can be expected that ectopic ossification in FOP can be suppressed or prevented for example by oral intake in a predetermined amount thereof at a predetermined feeling. The administration method is not limited to methods described above.

EXAMPLES

The present invention will now be described in detail by way of examples thereof.

<<I. Experimental Material and Experimental Method>>
<1. Formation of Skin-Derived Fibroblasts>
  (1) Fibroblasts were created from skin biopsy explants from FOP patients and normal subjects under informed consent by a protocol approved by Ethics committee.
  (2) Skin samples from patients and from normal subjects were finely cut and cultured in DMEM medium supplemented with 10% fetal bovine serum (FBS).
  (3) After emergence of fibroblasts was observed, the fibroblasts were grown to introduce a reprogramming gene. The grown fibroblasts were then put in a solution for freezing containing 10% DMSO+90% FBS and cryopreserved.
<2. Maintaining and Forming iPS Cells>
  (1) Human iPS cells were maintained, on MEF supporting cells treated with mitomycin C (MMC), in a human iPS medium containing DMEM/F12 (SIGMA-ALDRICH) supplemented with 20% KNOCKOUT (registered trademark) Serum Replacement (KSR, Invitrogen), 2 mM L-glutamine, $1 \times 10^{-4}$ M nonessential amino acid (NEAA, SIGMA-ALDRICH), $1 \times 10^{-4}$ M 2-mercaptoethanol (SIGMA-ALDRICH), 0.5% penicillin and streptomycin (NACALAI TESQUE, INC., Japan) and 5 ng/mL basic fibroblast growth factor (bFGF, Wako Pure Chemical Industries, Ltd., Japan).
  (2) iPS cells were formed from human-derived fibroblasts in a method described in N. Fusaki, H. Ban, A. Nishiyama, K. Saeki, M. Hasegawa, Proc. Jpn. Acad. Ser., B. Phys. Biol. Eci., 85, 348 (2009).
  (3) One day before infection, $5 \times 10^5$ human fibroblasts per well were seeded into a 6-well plate. Sendai virus (SeV) vector described below was then infected to the cells at a multiplicity of infection (MOI) of 3. That is, SeV vector including Oct3/4 gene, Sox2 gene, K1f4 gene, and c-Myc gene was created in accordance with a method described in N. Fusaki, H. Ban, A. Nishiyama, K. Saeki, M. Hasegawa, Proc. Jpn. Acad. Ser., B. Phys. Biol. Eci., 85, 348 (2009).
  (4) Seven days after the infection, the infected fibroblasts were collected using trypsin. $5.4 \times 10^{-4}$ cells per 60 mm petri dish or 1 to $2 \times 10^5$ cells per 100 mm petri dish were seeded onto the MEF supporting cells treated with MMC. On the next day, the medium was replaced with the human iPS cell medium. Culturing was continued, and colonies were observed until 30 days after infection.
  (5) Using media in which BMP-4 (10 ng/ml), BMP-6 (50 ng/ml) and BMP-7 (10 ng/ml) respectively were added to the above human iPS cell medium replaced on the 8th day after the infection, the cells were cultured until the 30th day, and thus an effect of bone morphogenetic proteins (BMP-4, 6 and 7) on iPS cell formation was confirmed. In addition, in a part of experiment, LDN-193189 (Stemgent, Inc.), an ALK2 kinase inhibitor, was added to the above human iPS cell medium in a concentration of 200 nM.

<3. Analyses by Immunoblotting and Immunoprecipitation>
  (1) In immunoblotting, cells were lysed in a lysis buffer (62.5 mM Tris-HCl, pH 7.4, 2% SDS, 0.05% 2ME, 10% glycerol, 0.00125% bromine). Obtained lysates were subjected to ultrasonic waves, and centrifuged for 10 minutes under conditions of 4° C. and 15000 rpm.
  (2) Obtained supernatants were subjected to SDS-PAGE, and target proteins were separated on a PVDF membrane.
  (3) The membrane was incubated with antiserum. Immune response bands were visualized by Enhanced Chemiluminescence detection (Perkin Elmer Co., Ltd.). Intensity of bands was evaluated by Image J software (NIH, USA).
  (4) In immunoprecipitation, 293T cells in which Smads were overexpressed, and KDM6B or LSD1 were lysed in RIPA buffer (50 mM Tris-HCl, pH 7.4, 1 mM EDTA, 150 mM NaCl, 1% NP-40, protease/phosphatase inhibitor cocktail). Obtained lysates were incubated with a required antibody at 4° C. overnight on a turntable. Protein G Resin was then added to the obtained lysate and this lysate was incubated at 4° C. for 2 hours on a turntable. The resin was washed with PMS three times and lysed in a buffer for Western blotting.

<4. Chromatin Immunoprecipitation and ChIP-ChIP Analysis>
  (1) Proteins were fixed (cross-linked) to DNA by an action of 1% formaldehyde on cells. Obtained lysates were incubated with an anti-histone methyl antibody. Purified DNA fragments were amplified by PCR.
  (2) In ChIP-ChIP analysis, FOP-derived fibroblasts were lysed in RIPA buffer. Obtained lysates were incubated with anti-FLAG affinity gel (A2220, SIGMA-ALDRICH) at 4° C. overnight on a turntable. The obtained gel was washed with TBS 5 times. To this gel, RIPA buffer containing 100 ng/ml FLAG peptide (F3290, SIGMA-ALDRICH) was added. The obtained gel was incubated at 4° C. for 2 hours on the turntable. Obtained mixtures were washed with TBS three times. To the mixtures, TBS buffer containing 500 ng/ml 3×FLAG peptide (F4799, SIGMA-ALDRICH) was added. The obtained mixtures were incubated at 4° C. for 2 hours on a turntable. This operation was repeated three times.

<<II. Experimental Results>>
<Experiment 1. Investigations of Methylation of Histone H3 in FOP-Derived Fibroblasts>
  (1) FOP-derived fibroblasts were induced into iPS cells, and methylation of histone H3 was examined. As an object for comparison, normal fibroblasts were used.

Figure 1:
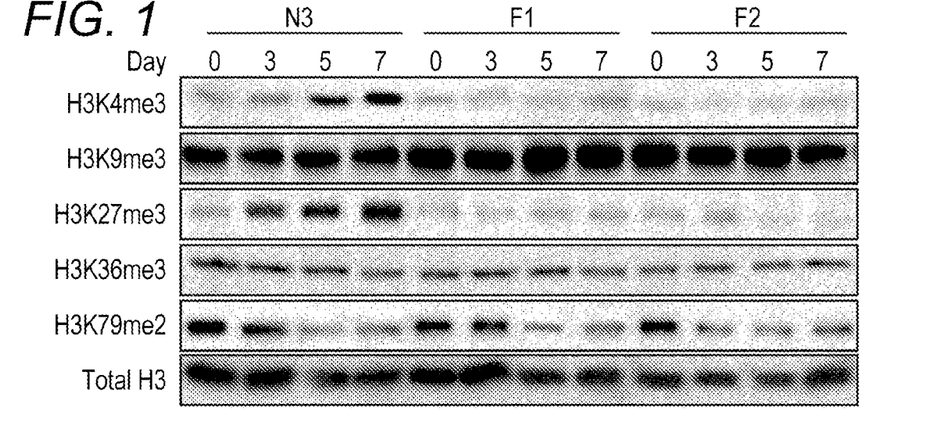
FIG. 1 is a drawing showing methylation of histone H3 in induction of iPS cells in a case of FOP patients.

(2) Results are shown in FIG. 1. In the normal fibroblasts (N3), intensity of bands of K4 and K27 of histone H3 increased as induction into iPS cells progressed.
(3) On the other hand, in the FOP-derived fibroblasts (F1, F2), changes in the bands of K4 and K27 of histone H3 were not observed.
(4) In addition, differences in K9, K36 and K79 were not observed between the bands of normal fibroblasts and the bands of FOP-derived fibroblasts.
(5) These results have suggested that one of the reasons why it is difficult to establish induction of FOP-derived fibroblasts into iPS cells is abnormal methylation of K4 and K27 of histone H3.

<Experiment 2. Comparison of Differentiation to Osteoblasts by BMP6 Stimulation in the Presence of Serum>

Figure 2:
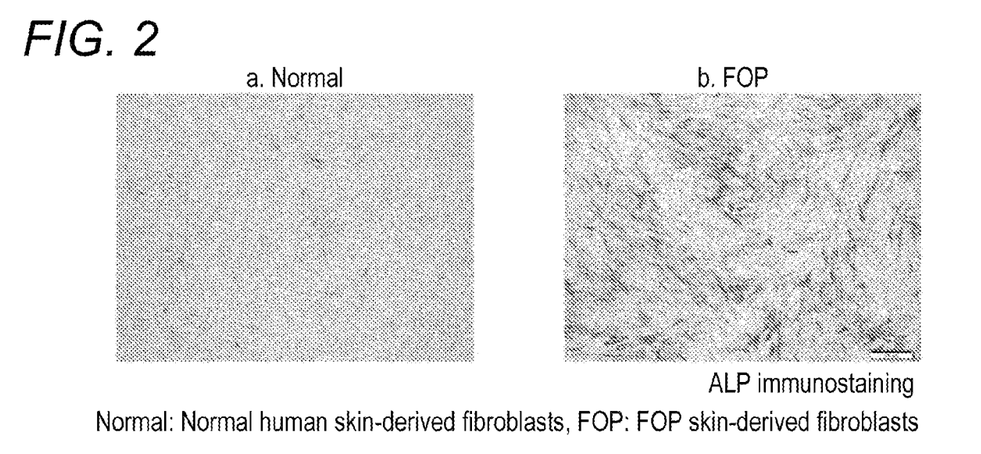
FIG. 2 is an immunostaining image in which a differentiation of FOP-derived fibroblasts to osteoblasts by BMP6 stimulation in the presence of serum is compared and investigated.

(1) Differentiation of FOP-derived fibroblasts to osteoblasts in the presence of serum depending on the presence or absence of BMP6 was investigated by comparison with differentiation of normal subject-derived fibroblasts to osteoblasts.
(2) Results of immunostaining by alkali phosphatase (ALP), an osteoblast marker, are shown in FIG. 2.
(3) In the normal subject-derived fibroblasts (Normal), almost all cells were not stained. Accordingly, it has been found that induction of differentiation to osteoblasts does not proceed (FIG. 2a). On the other hand, in the FOP-derived fibroblasts (FOP), cells were significantly stained compared to those in the normal subject-derived fibroblasts. Accordingly, it has been found that osteoblast induction easily proceeds (FIG. 2b).

<Experiment 3. Comparison of PAR1 Expression by BMP6 Stimulation in the Presence of Serum>

Figure 3:
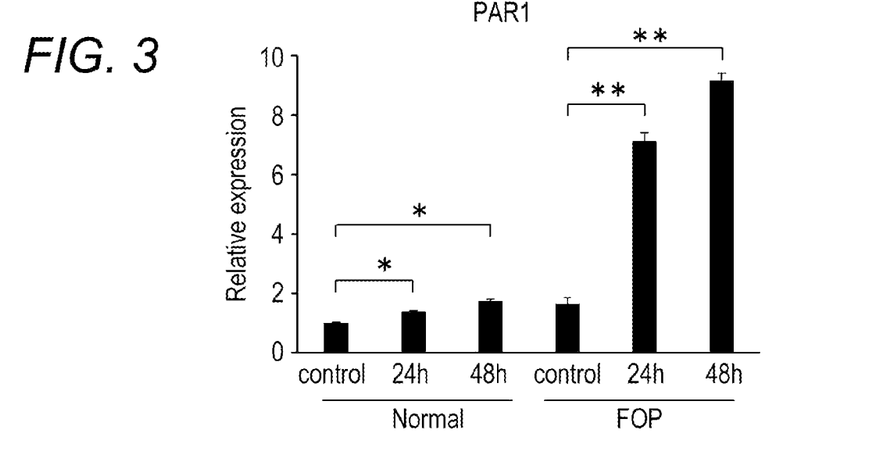
FIG. 3 is a graph in which an mRNA expression level of PAR1 in FOP-derived fibroblasts by BMP6 stimulation in the presence of serum is compared and investigated.

(1) This experiment was performed to investigate whether a change in PAR1 expression level in FOP-derived fibroblasts in the presence of serum was observed depending on the presence or absence of BMP6 by comparison with PAR1 expression level in normal subject-derived fibroblasts.
(2) Results are shown in FIG. 3. FIG. 3 is a graph showing results that mRNA expression levels in respective fibroblasts treated with BMP6 (50 ng/mL) at each time was analyzed by qPCR.
(3) Increase in expression of PAR1 in the normal subject-derived fibroblasts (Normal) significantly increased by BMP6 stimulation over time. However, the increase was mild. On the other hand, in the FOP-derived fibroblasts (FOP), a remarkable increase was observed compared to that in the normal subject-derived fibroblasts.

<Experiment 4. Comparison of Differentiation to Osteoblasts by BMP Stimulation and Stimulation of an Agonist of PAR1 in the Absence of Serum>

Figure 4:
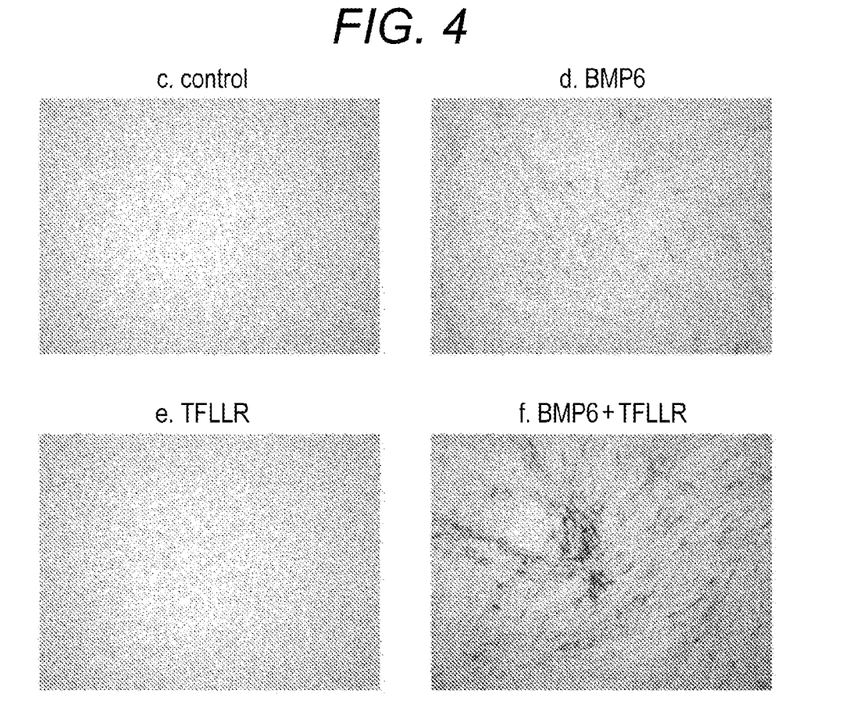
FIG. 4 is an immunostaining image in which a differentiation of FOP-derived fibroblasts to osteoblasts by BMP6 stimulation or TFLLR stimulation in the absence of serum is compared and investigated.
Figure 5:
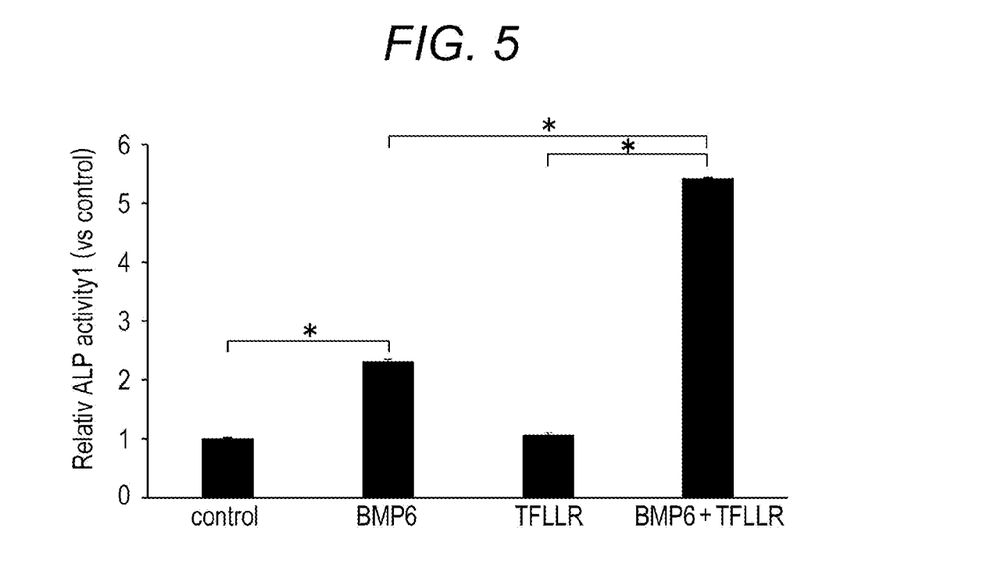
FIG. 5 is a graph in which a differentiation of FOP-derived fibroblasts to osteoblasts by BMP6 stimulation or TFLLR stimulation in the absence of serum is compared and investigated by measuring ALP activity.

(1) Differentiation of FOP-derived fibroblasts to osteoblasts in the absence of serum depending on the presence or absence of BMP6 was investigated by comparison with differentiation of normal subject-derived fibroblasts to osteoblasts. In addition, a similar investigation was carried out in the presence or absence of TFLLR, an agonist of PAR1.
(2) Results of immunostaining by ALP are shown in FIG. 4. In addition, the results obtained by comparing ALP activity of samples with ALP activity of control are shown in FIG. 5.
(3) In the FOP-derived fibroblasts cultured in the absence of serum, ALP expression was hardly observed (FIG. 4c). Accordingly, it has been found that the differentiation of FOP-derived fibroblasts to osteoblasts is hardly observed in the absence of serum.
(4) In the presence of BMP6, the ALP expression was observed, and the ALP activity also significantly increased compared to the ALP activity of control (FIGS. 4d and 5). Accordingly, it has been found that differentiation to osteoblasts proceeds by BMP6 stimulation in the absence of serum. However, when this result is compared to the result in the investigations in the presence of serum (FIG. 2b), it can be said that differentiation to osteoblasts is weak.
(5) In the presence of TFLLR, an agonist of PAR1, the ALP expression was hardly observed, and the ALP activity was also low (FIG. 4e and FIG. 5). Accordingly, it has been found that differentiation to osteoblasts hardly proceeds by TFLLR stimulation in the absence of serum.
(6) In the presence of both BMP6 and TFLLR, the ALP expression increased, and the ALP activity largely increased (FIG. 4f and FIG. 5). Accordingly, it has been found that differentiation to osteoblasts largely proceeds by stimulation of two molecules, BMP6 and TFLLR, in the absence of serum.
(7) These results have showed that the differentiation of FOP-derived fibroblasts to osteoblasts is induced in association with two molecules, BMP6 and PAR1.

<Experiment 5. Comparison of Differentiation to Osteoblasts in the Absence of Serum when Using Each Inhibitor>

Figure 6:
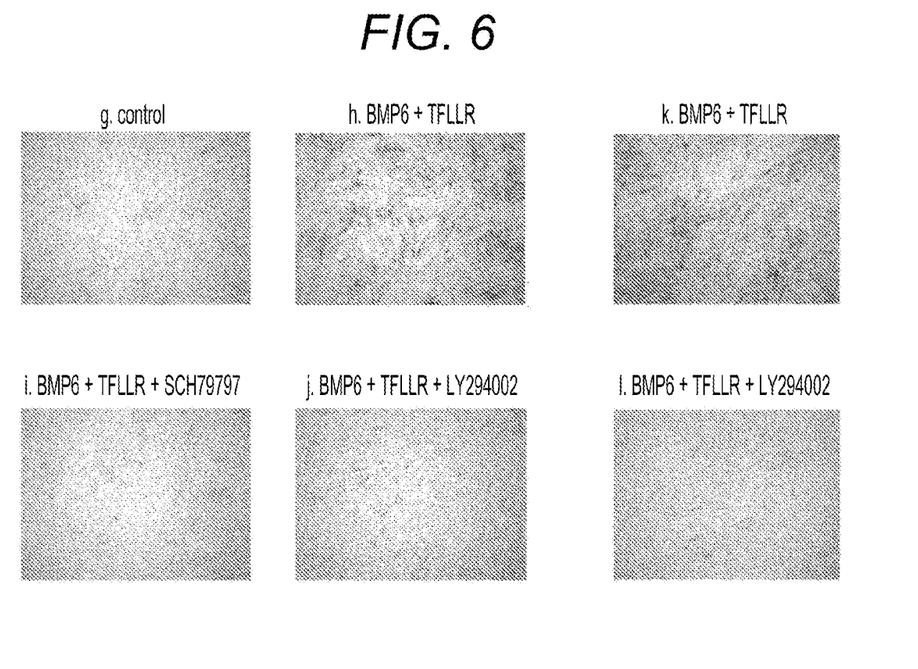
FIG. 6 is an immunostaining image in which a differentiation of FOP-derived fibroblasts to osteoblasts by a PAR1 inhibitor or a PI3K inhibitor in the absence of serum is compared and investigated.
Figure 7:
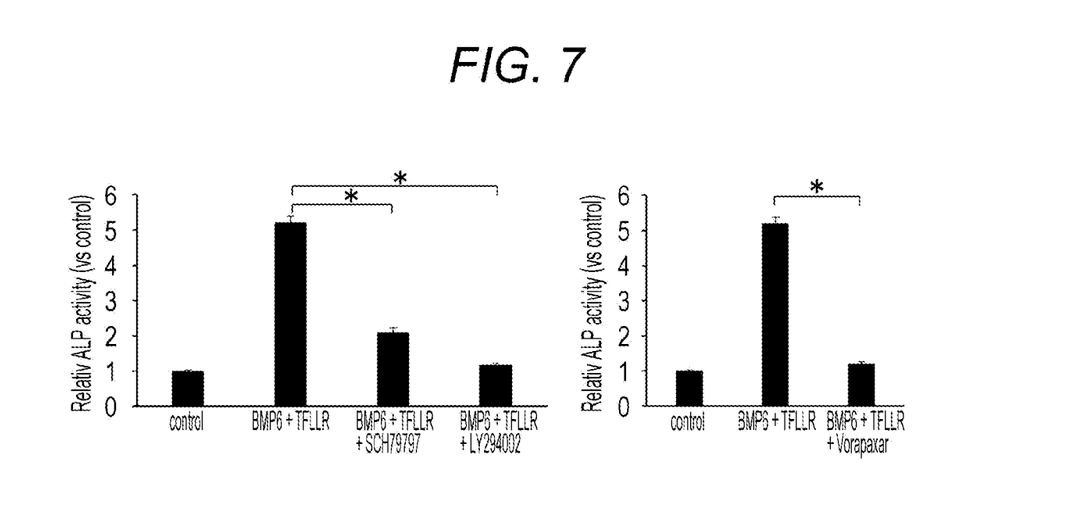
FIG. 7 is a graph in which a differentiation of FOP-derived fibroblasts to osteoblasts by a PAR1 inhibitor or a PI3K inhibitor in the absence of serum is compared and investigated by measuring ALP activity.

(1) In order to examine how PAR1 inhibitors (SCH79797, Vorapaxar) and a PI3K inhibitor (LY294002) affect the differentiation of FOP-derived fibroblasts to osteoblasts, investigations were carried out using these inhibitors.
(2) Results of immunostaining by ALP are shown in FIG. 6. In addition, the results of comparison of the ALP activity of samples and the ALP activity of control are shown in FIG. 7.
(3) As with the results in Example 4, in the absence of serum, the differentiation of FOP-derived fibroblasts to osteoblasts hardly proceeded without stimulation of either BMP6 or TFLLR (FIG. 6g), whereas differentiation to osteoblasts largely proceeded with stimulation by these molecules (FIGS. 6h and 6k).
(4) On the other hand, both the ALP expression and the ALP activity largely decreased in the presence of SCH79797 (200 nM) or Vorapaxar (1 μM), either of which is a PAR1 inhibitor (FIGS. 6i and 6l, FIG. 7). Similarly, both the ALP expression and the ALP activity also largely decreased in the presence of LY294002 (10 μM), a PI3K inhibitor (FIG. 6j, FIG. 7). These results have showed that an inhibition of PAR1 leads to suppression of differentiation of FOP-derived fibroblasts to osteoblasts, and that suppression of signal transduction of PI3K downstream of PAR1 leads to the suppression of differentiation of FOP-derived fibroblasts to osteoblasts.
(5) These results have showed that a PAR1 inhibitor can be expected to treat ectopic ossification in FOP.

<Experiment 6. Verification of PAR1 Inhibitors by an Animal Test>

(1) Investigations were carried out to examine how a PAR1 inhibitor (Vorapaxar) affects suppression of ectopic ossification in mice.
(2) NOG mice were used as an in vivo model. iPS cells created from fibroblasts derived from FOP patients were implanted into a testicle. Accordingly, teratomas were formed. In the in vivo model, the teratomas grow after implantation, and ossification proceeds in the teratomas after 9 weeks, and bone volume increases. Because of this, Vorapaxar (0.2 mg/kg/day) was intraperitoneally administered once daily from 9 weeks after implantation. A solution not containing Vorapaxar as an active ingredient (vehicle) was intraperitoneally administered as an object for comparison in a similar manner.

Figure 8:
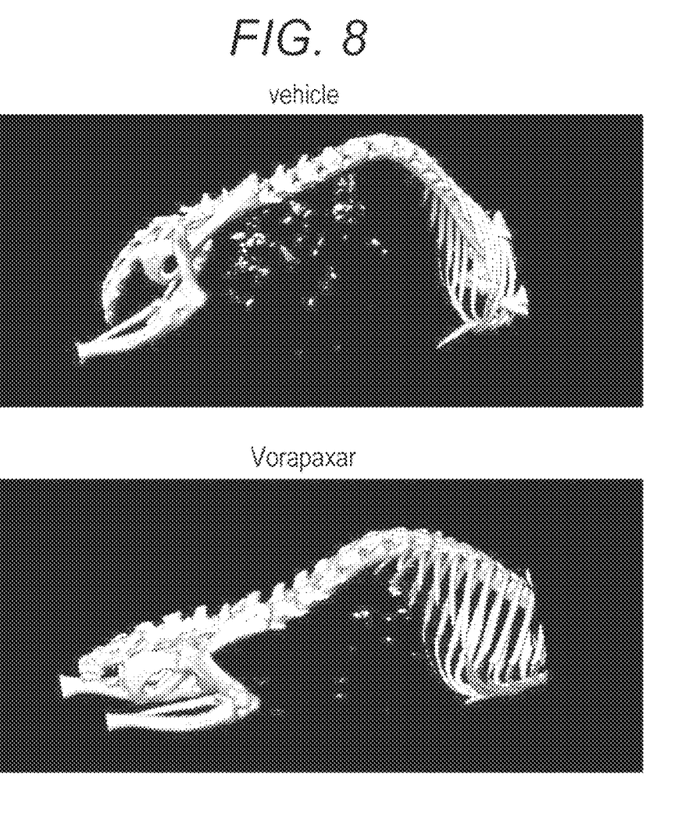
FIG. 8 is an image in which an effect of a PAR1 inhibitor (Vorapaxar) on ectopic ossification is compared and investigated with CT by using an in vivo model.
Figure 9:
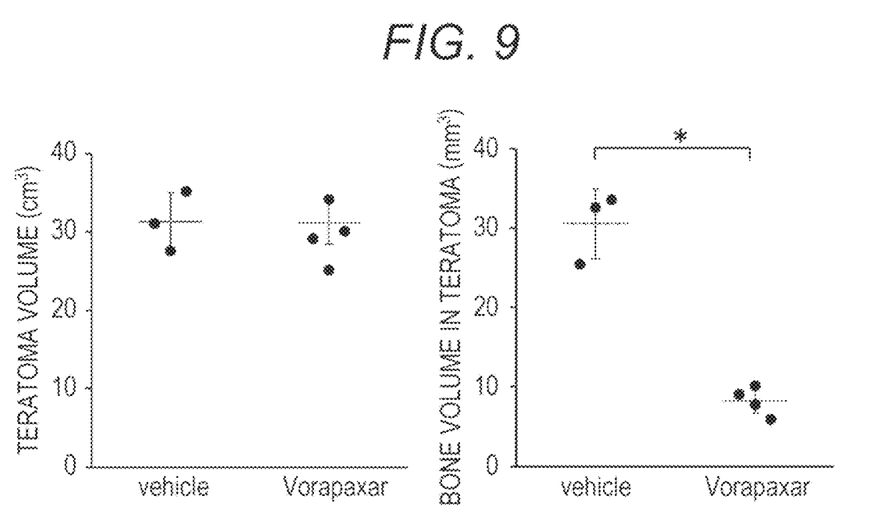
FIG. 9 is a graph in which an effect of a PAR1 inhibitor (Vorapaxar) on ectopic ossification is compared and investigated with graphs by using an in vivo model.

(3) Results are shown in FIG. 8 and FIG. 9. FIG. 8 shows CT images of the in vivo model. FIG. 9 is a graph showing the teratoma volume and the bone volume in the teratomas calculated from CT images.

(4) In individuals to which vehicle had been administered, bones were found everywhere in the teratomas formed in testicle after 2 weeks of Vorapaxar administration (FIG. 8, upper). On the other hand, it was verified that bones found everywhere in individuals to which Vorapaxar had been administered were notably less than the bones found everywhere in the individuals to which vehicle had been administered (FIG. 8, lower).

(5) In addition, when the volume of the teratomas artificially formed was calculated from CT images, a significant difference in the teratoma volume was not observed between the individuals to which vehicle had been administered and the individuals to which Vorapaxar had been administered (FIG. 9, left). On the other hand, when the bone volume was calculated, the bone volume in the individuals to which Vorapaxar had been administered was about one third of the bone volume in the individuals to which vehicle had been administered, which largely and significantly decreased (FIG. 9, right).

(6) These results have showed that a bone observation and a decrease in bone volume in the individuals to which Vorapaxar have been administered are caused not by a difference in the growth degree of teratoma but by exhibiting a medicinal effect of Vorapaxar, a PAR1 inhibitor. These results have also showed by an animal test that a PAR1 inhibitor can be expected to treat ectopic ossification in FOP.

<Experiment 7. Verification of Suppression of PAR1 Function by an Animal Test>

(1) Investigations were carried out to examine how artificial suppression of PAR1 function affects suppression of ectopic ossification in mice.

(2) An in vivo model was created in a similar manner as in Experiment 6. In accordance with previous reports, siRNA (siPAR1) which suppresses PAR1 expression was created, and siPAR1 was intraperitoneally administered once daily from 9 weeks after teratoma implantation. siRNA of Luciferase (siLuciferase) and siRNA (siALK2-R206H) were intraperitoneally administered as objects for comparison in a similar manner. siLuciferase does not affect a living body. siALK2-R206H suppresses expression of ALK2 already known as an ossification factor.

Figure 10:
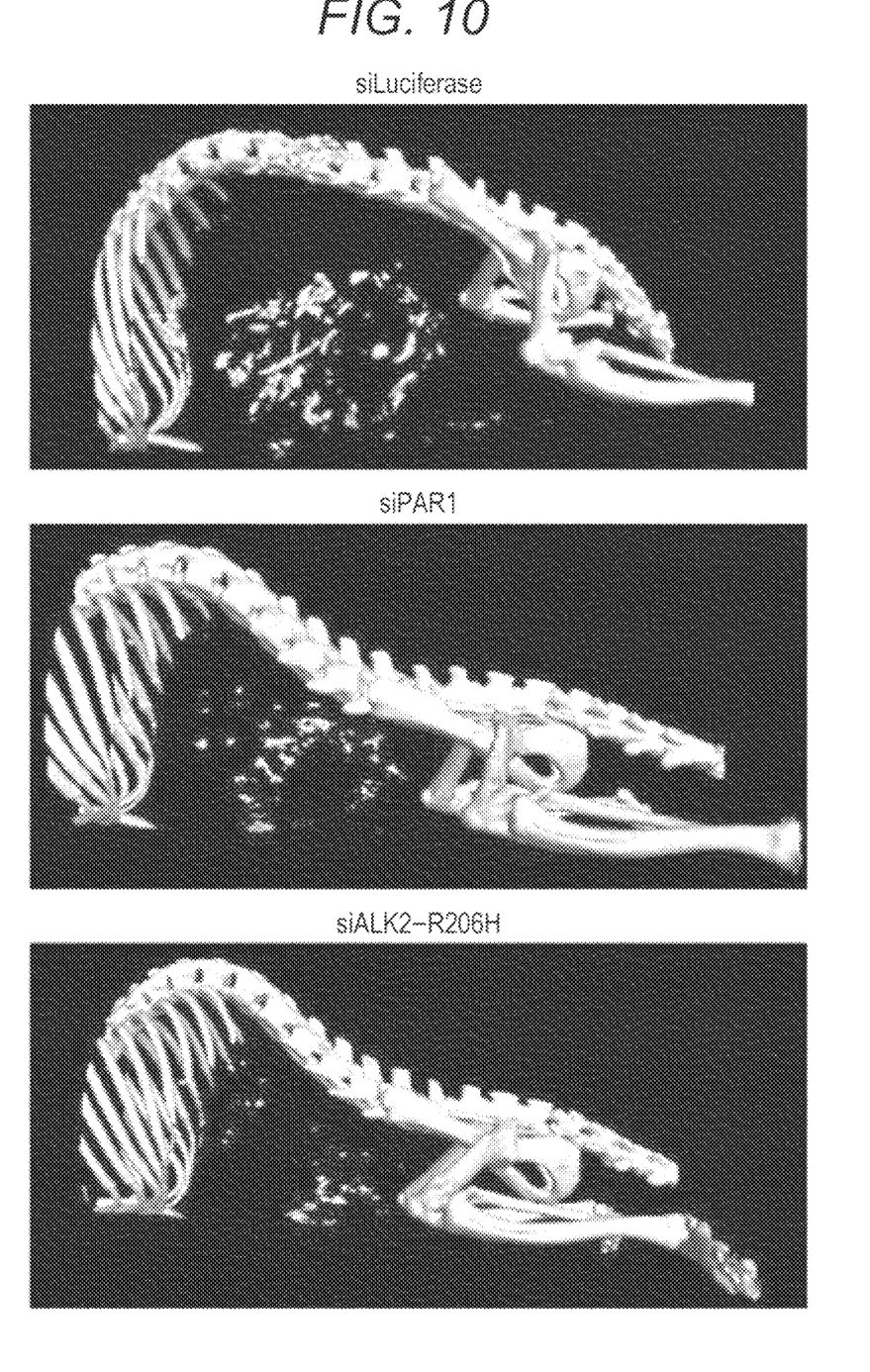
FIG. 10 is an image in which CT images of an in vivo model are compared and investigated, each siRNA having been administered to the in vivo model.
Figure 11:
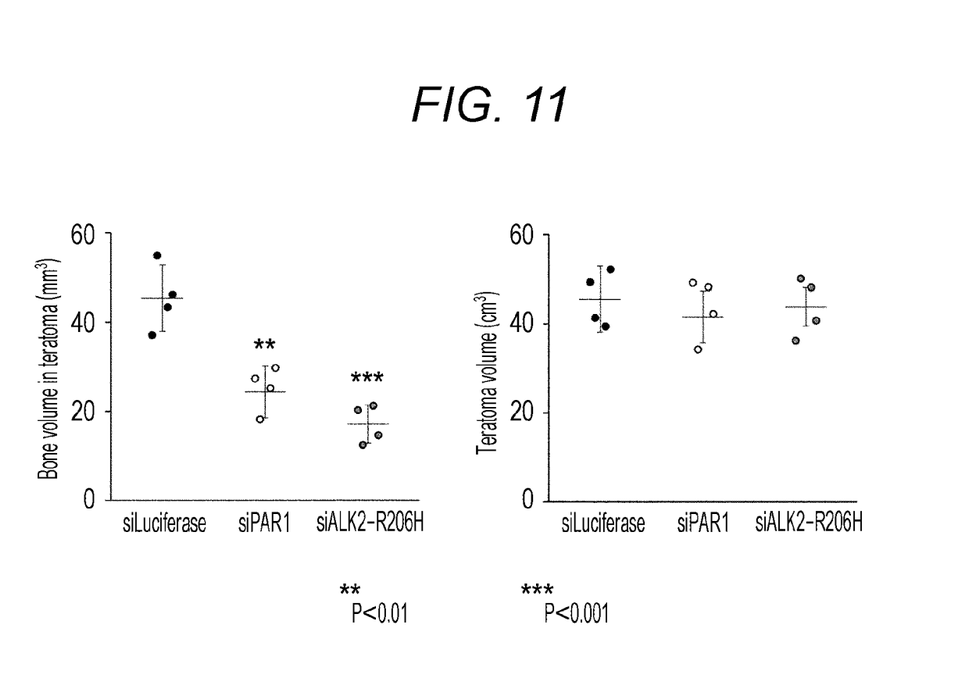
FIG. 11 is a graph in which teratoma volume and bone volume in teratomas calculated from CT images are compared and investigated.

(3) Results are shown in FIG. 10 and FIG. 11. FIG. 10 shows CT images of the in vivo model. FIG. 11 is a graph showing teratoma volume and bone volume in teratomas calculated from CT images.

(4) In individuals to which siLuciferase had been administered, bones were found everywhere in the teratomas formed in testicle after 2 weeks from administration. On the other hand, it was verified that bones found everywhere in individuals to which siPAR1 had been administered and in individuals to which siALK2-R206H had been administered were notably less than bones found everywhere in the individuals to which siLuciferase had been administered.

(5) In addition, when the volume of the teratoma artificially formed was calculated from CT images, a significant difference in the teratoma volume was not observed between the individuals to which siLuciferase had been administered, the individuals to which siPAR1 had been administered, and the individuals to which siALK2-R206H had been administered. On the other hand, when the bone volume was calculated, the bone volumes in the teratomas significantly decreased in the individuals to which siPAR1 had been administered and in the individuals to which siALK2-R206H had been administered, as compared to that in the individuals to which siLuciferase had been administered.

(6) These results have showed that a bone observation and a decrease in bone volume in the individuals to which siPAR1 has been administered are caused not by a difference in the growth degree of teratoma but by a result of suppression of the expression of PAR1 function, the suppression being carried out by siRNA. This has also showed by an animal test that the inhibition of expression of PAR1 function can be expected to treat ectopic ossification in FOP.

The invention claimed is:

1. A method for treating or suppressing ectopic ossification, comprising treating or suppressing ectopic ossification by administering a Protease-Activated Receptor-1 (PAR1) inhibitor to a subject having a disease involving the ectopic ossification which occurs by an inflammation due to an injury.

2. The method according to claim 1, the PAR1 inhibitor is a PAR1 antagonist.

3. The method according to claim 2, the PAR1 antagonist is ethyl [(1R,3aR,4aR,6R,8aR,9S,9aS)-9-{(1E)-2-[5-(3-fluorophenyl)pyridin-2-yl]ethen-1-yl}-1-methyl-3-oxodo-decahydronaphtho[2,3-c]furan-6-yl]carbamate or a salt thereof.

4. The method according to claim 1, wherein the ectopic ossification is a symptom caused by fibrodysplasia ossificans progressiva.

5. A method for treating or suppressing ectopic ossification, comprising administrating a Protease-Activated Receptor-1 (PAR1) inhibitor to a subject in which a differentiation from a fibroblast to an osteoblast is induced by bone morphogenetic protein (BMP) stimulation.

6. The method according to claim 5, the BMP stimulation is BMP 4, 6 or 7 stimulation.

7. The method according to claim 5, the BMP stimulation is BMP 4 or 6 stimulation.

8. The method according to claim 5, the BMP stimulation is BMP 6 stimulation.

* * * * *